United States Patent [19]

Arnaud et al.

[11] Patent Number: 4,642,294
[45] Date of Patent: Feb. 10, 1987

[54] PROCESS FOR EVALUATING THE STATE OF THE SURFACE OF KERATINOUS FIBRES AND A COMPOSITION FOR MAKING USE OF THIS PROCESS

[75] Inventors: Jean-Claude Arnaud, Paris; Pierre Boré, Montfermeil, both of France

[73] Assignee: L'Oreal, Paris, France

[21] Appl. No.: 817,604

[22] Filed: Jan. 10, 1986

[30] Foreign Application Priority Data

Jan. 16, 1985 [FR] France ................................ 85 00566

[51] Int. Cl.⁴ .......................................... G01N 31/00
[52] U.S. Cl. ...................................... 436/5; 436/119; 436/164; 436/86
[58] Field of Search ................. 436/2, 5, 86, 119, 164, 436/175, 178

[56] References Cited

U.S. PATENT DOCUMENTS 3,992,149 11/1976 Wang .................................. 436/164
4,421,859 12/1983 Boré et al. ............................ 436/86

FOREIGN PATENT DOCUMENTS 1053003 11/1983 U.S.S.R. ................................ 436/86

*Primary Examiner*—Charles Hart
*Attorney, Agent, or Firm*—Cushman, Darby & Cushman

[57] ABSTRACT

According to this process, (a) a compound capable of entering the surface interstices of the keratinous fibres is chosen; which is capable of producing, in an aqueous medium, a solution which is colored naturally or capable of being colored by a development, and capable, under the conditions of the process, of being stable and maintained at a pH such that no ionic charge appears; (b) an aqueous immersion solution containing the compounds chosen is prepared; (c) a specimen of the fibres to be studied is immersed therein to produce an "uptake" of the compound on the fibres, which is a function of their surface state; (d) the specimen is withdrawn from the solution and the excess of solution saturating the fibres is removed; (e) the compound present on the fibres is extracted by immersing the latter in at least one aqueous bath at the same pH as that of the aqueous immersion solution to obtain an extraction solution which is colored or whose color is developed in a step (f); and (g) the state of the surface of the fibres is deduced from the quantity of the compounds present in the extraction solution.

24 Claims, No Drawings

PROCESS FOR EVALUATING THE STATE OF THE SURFACE OF KERATINOUS FIBRES AND A COMPOSITION FOR MAKING USE OF THIS PROCESS

The present invention relates to a process for evaluating the state of the surface of keratinous fibres, especially human hair and body hair. It also relates to a composition for making use of this process.

Experts in keratinous fibres, be they research workers or practitioners such as hairdressers or wig makers, often need to evaluate quickly the quality of the keratinous fibre with which they are working. This evaluation is generally carried out by the expert from the standpoint of needing to know how a chemical or cosmetic treatment, such as a reduction, oxidation, bleaching, permanent-waving, coloring, and the like, will be received and withstood by the hair or the body hair.

Most certainly, by relying on his or her experience, the expert can assess the state of the surface of keratinous fibres according to their appearance and their feel. Howevr, this assessment is not rigorous, because it is often partial, frequently subjective, and generally non-quantitative. It is therefore difficult to rely on such a method to compare the states of the surface of different keratinous fibres with each other.

The known state of the art relates to a closely related, but different, field, namely that of the wool industry. It is possible, in fact, to refer to a number of methods which are described in the literature, and which are intended for the evaluation of the quality of the wool after industrial processing.

First of all, reference can be made to the tests which reveal the deterioration due to chlorination and to mechanical or alkaline treatments. These are, in particular, the Kiton G red coloring test, described by Carter and Consden in J. Text. Inst. (1946) 37, T 227, the methylene blue coloring test, described by Whewell and Austerlitz in J. Soc. Dy. Col (1943) 59,45, the indigo carmine coloring test, described by Grieve in J. Text. Inst. (1946) 37, T 267, the orange II absorption test, described by MacLaren in Arch. Biochem. Biophys. (1960)80, and the Lacto blue (cotton blue IV in a lactic acid-phenol solution) test, described by Robinet and Bielen in Ann. Sect. Text. Belge (1956) 4-12,31.

Secondly, reference can also be made to tests which reveal ruptures of peptide bonds and of disulphide bonds. These are, in particular, the alkaline solubility test described by Harris and Smith in Amer. Dyest. Rep. (1936) 25,542, the test for solubility in phenol-thioglycolic acid, described by Speakman and Menkart in Bull. Inst. Text. Fr (1952) 30,315 and the test for solubility in urea-bisulphite, described by Lees and Elsworth in J. Soc. Dy. Col. (1954)70,354.

All these tests require several hours, or even more than a day, to provide an answer which is frequently very partial and of limited benefit to the hairdresser.

Still on the subject of evaluating the quality of wool which has been subjected to industrial processing, there are also known methods for investigating the porosity, namely the adsorption of para-nitrophenol, which is described by Jovanovic in App. Pol. Symp. (1971) 915, and the adsorption of dextrans, described by Shutz in S. Int. Wool. Text. Res. Conf. (1975) Vol. II, 446.

These methods of studying the porosity employ complex techniques and require costly apparatus. They, too, cannot be put into general use in hairdressing salons.

It is known, furthermore, that the keratinous fibre reacts with treatment solutions both as a result of the excess of ionic charges present on the surface of these fibres and as a result of the porosity of this surface, due to sensitization of the fibre.

The term "porosity" is here understood to mean the totality of the physical surface phenomena whose common characteristic is that reactant compounds are allowed to pass freely through the cuticle layers of the keratinous fibres.

Thus, for example, the document GB-A-20277 195 relates to a process for evaluating the ionic state of hair by using nitrobenzene derivatives in an acidic medium. These dyes are used as adjuvants or dyeing toners which, under the chosen conditions, are incapable of changing their color as a function of the pH, and their intensity, when they do not react with the hair.

The applicants have found that there is a close correlation between, on the one hand, the kinetics of exchange between the uncharged compounds and the keratinous fibres and, on the other hand, the surface porosity of the fibres, in other words, of their degree of surface sensitization. Based on this finding, it has developed a process for evaluating the quality of the surface of keratinous fibres, which consists in causing uncharged compounds, which are colored or whose color can be readily developed, to be "taken up" through the surface layers of the said fibres, by immersing the fibres to be studied in a solution containing the said compounds, and in then extracting into a solution the compounds which were "taken up" on the keratinous fibres, the quantity of compounds present in the extraction solution being a function of the porosity and, as a result, of the state of the surfaces of the keratinous fibres.

The compound employed must meet the following conditions:

firstly, the compound must, in addition to the abovementioned conditions, have a size which enables it to enter the interstices of the surface layers of the keratinous fibres;

secondly, the compound must be generally soluble in an aqueous medium, to make it possible to produce solutions which have a color, naturally or after development, possessing a sufficient intensity;

thirdly, the compound must be stable under the conditions of application of the process;

fourthly, the compound must carry no ionic charge under the conditions of application of the process, so as not to interfere with the measurement of the ionic state of the hair.

Furthermore, since the principle which underlies the invention is that the kinetics of uptake of the compound solely on the surface layers of the keratinous fibres are correlated with the state of the surface of these fibres, the duration of the operation which consists in producing the "uptake" of the compound on the fibres must be controlled so that the compound does not reach the deeper layers of the keratinous fibres.

Moreover, the extraction of the compound which has been "taken up" by the keratinous fibres must be carried out under the same pH conditions as the immersion, for the abovementioned reasons. The extraction solution contains the quantity of compounds which have been taken up on the surface of the keratinous fibres, quantities which correspond to a determined surface delay. Since it is colored naturally or capable of being colored after development, it is easy to compare this color (or the absorbance) to that of a range of solutions of the same compound at different concentrations, each of these colors being associated with a well-determined state of the surface, in order that the state of the surface of the keratinous fibres being investigated can then be known.

The subject of the present invention is therefore a process for evaluating the state of the surface of keratinous fibres, especially of human hair and body hair, characterized in that:

(a) a compound having an overall spatial size such that it can enter the interstices present at the surface of the keratinous fibres is chosen, the said compound being capable of producing, in an aqueous medium, a solution which is naturally colored or capable of being colored by a development process, and capable, under the conditions in which the process is carried out, of being stable and being maintained at a pH such that no ionic charge appears;

(b) an aqueous immersion solution containing the compounds chosen is prepared;

(c) a specimen of the keratinous fibres whose surface state is to be evaluated is immersed in the said solution, to produce an "uptake" of the compound on the said fibres, which is a function of the state of the surface of the latter;

(d) the keratinous fibres specimen is removed from the said solution and the excess of the said solution with which the fibres are saturated is removed by fast washing or dewatering.

(e) the compound is extracted from the fibres of the said specimen by immersing the fibres in at least one aqueous bath whose pH is substantially identical to that of the aqueous immersion solution, to obtain an extraction solution which is correspondingly colored or capable of being colored by a development;

(f) the color of the extraction solution is developed, where appropriate,; and (g) the state of the surface of the said keratinous fibres is deduced from the quantity of compounds present in the said extraction solution.

Preferably, the compound which is chosen has an overall size of $10^{-3}\mu$; it is sufficiently soluble in an aqueous medium to permit the preparation of a solution of the said compounds containing at least 0.01 mole per liter; and it is capable of giving, in an aqueous medium, a solution which is capable of absorbing in the visible and/or in the ultraviolet, naturally or after colorimetric development, and whose molar absorbance, measured at the wavelength of the maximum of the absorption spectrum of the said solution which is colored naturally or after colorimetric development, is at least equal to 1500.

A compound which meets all these criteria is advantageously chosen from the benzene and naphthalene series.

By way of preferred examples, there are mentioned:
as compounds which do not require development: a compound of formula:

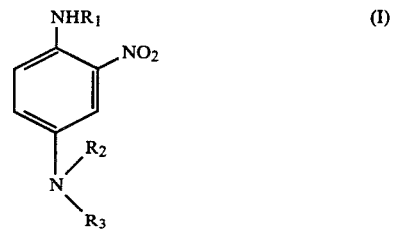

in which formula:
$R_1$ denotes H, $CH_2CH_2OH$, $CH_2CH_2NH_2$, $CH_3$;
$R_2$ and $R_3$ denote, independently, H and $CH_2CH_2OH$;

as compounds which require a development: a compound chosen from the group consisting of 1,3-dihydroxynaphthalene, α-naphthol, 2,6-dimethylphenol and 2,4-diaminoanisole sulphate.

Among the abovementioned compounds which do not require development, those more particularly preferred are 2-nitro-para-phenylenediamine, indicated in the Colour Index under the name "CI 76070", 2-N-(β-hydroxyethyl)amino-5-N,N-bis(β-hydroxyethyl)aminonitrobenzene, mentioned in the Colour Index under the name "HC Blue 2", 2-N-(β-aminoethyl)amino-5-N,N-bis(β-hydroxyethyl)aminonitrobenzene, 2-N-methylamino-5-N,N-bis(β-hydroxyethyl)aminonitrobenzene, and 4-N-(β-hydroxyethyl)amino-3-nitroaniline.

In accordance with the preferred manner of making use of the present invention, in step (b) of the process, an aqueous solution of the chosen compound is prepared, containing a third solvent, the weight ratio (aqueous part/third solvent) being at least equal to 80/20; the weight ratio (aqueous part/third solvent) is advantageously of the order of 90/10. Ethanol is preferably chosen as third solvent. The third solvent enables the solubility of the compound in the solution used to be improved, to produce "the uptake" of this compound on the keratinous fibres. The quantity of third solvent cannot, however, exceed the value of 20% by weight relative to the total weight of the composition, because too high a quantity of third solvent modifies the state of the surface of the keratinous fibre significantly by contraction of the latter, which interferes with the correct application of the process.

Furthermore, since it is essential that, during the entire application of the process, the compound is maintained at a pH such that no positive or negative ionic charge appears, an aqueous solution of the above-mentioned compound is advantageously prepared in step (b), whose aqueous part consists of a buffer solution. Preferably, an aqueous solution is prepared, whose pH is at least two pH units below or above the $pK_a$. Depending on the ionizable groups present in the compound, use is advantageously made either of pH 10 buffers (carbonate, borate, ammoniacal buffer, and the like), or of buffers below pH 5 (acetate, citrate, and the like).

In accordance with a preferred embodiment of the present invention, in step (c), the specimen of keratinous fibres is immersed, in a proportion of approximately 100 mg of fibres per 2 to 10 ml of solution for at most 20 minutes, preferably for a time of between 2 and 5 minutes, and at a temperature below 50° C., preferably at a temperature close to ambient temperature.

It has been seen that, when a keratinous fibre is immersed in a solution such as defined above, the kinetics of the "uptake" of the compound on the keratinous fibre depend on the state of the surface of the latter. In connection with this observation, the applicants have found that, if the immersion in step (c) lasts too long (over 20 minutes), the quantity of compound which can be extracted from the hair is then substantially the same, whatever the state of the surface of the fibre, and it has found that, if the immersion of the keratinous fibre lasts for less than 20 minutes, and preferably from 2 to 5 minutes, the quantity of dye which can be extracted from the keratinous fibre is then directly related to the quality of the surface of the cuticle of this keratinous fibre.

In accordance with a preferred embodiment of the present invention, use is made, for the extraction in step (e), of at least one bath of the same buffer solution as that which has been used to prepare the immersion solution, or at least one bath of water brought to the same pH as that of the buffer solution which has been used to prepare the immersion solution. The extraction is preferably carried out for a period of at least 3 minutes, for example 5 minutes or even longer.

In accordance with a preferred embodiment of the present invention, in step (g) the extraction solution which is colored, or after development of its color, is compared to a range of dilutions of a concentrated solution of the compound in the same medium as that which has been used for the extraction, or the extraction solution which is colored, or after development of its color, is analysed by means of a spectrophotometer or a colorimeter set at the wavelength of the maximum of the absorption spectrum of the extraction solution, which is either colored or after development of its color.

Next, the results are expressed on a colorimetric scale (absorbance scale), on a scale of concentrations of the compound or on an empirical scale after calibration. In the latter case, especially when hair is involved, the calibration is carried out, for example, using a natural hair or using a highly sensitized hair.

By way of example, where the hair which is to be found on heads in a hairdressing salon is concerned, whatever the way that the results are expressed, the latter can be placed on a sensitization scale which is generally indicated in the following Table in which sensitization decreases from top to bottom and a chained line indicates an overlap of values between adjacent entries.

| SENSITIZATION | HAIR DESCRIPTION |
|---|---|
| HIGH SENSITIZATION | hair which has had several treatments bleached, permanent-waved, natural permanent-waved 2 or 3 times straightened hair bleached-dyed hair permanent-waved-dyed hair |
| MEDIUM SENSITIZATION | natural hair, permanent-waved once bleached hair |
| LOW SENSITIZATION | natural hair and dyeing shampoo natural hair |

Another subject of the present invention is a composition for making use of the process defined above, this composition being characterized in that it consists of an aqueous solution maintained at a pH such that no ionic charge appears, of a compound chosen from those which, on the one hand, have an overall spatial size which does not exceed the maximum dimension of the interstices present at the surface of the keratinous fibres, which, furthermore produce a solution which is naturally colored or capable of being colored by means of a development, and which, lastly, are stable in the said solution and capable of being maintained at the pH defined above.

Advantageously, the compound has the characteristics indicated above.

The advantageous characteristics of this composition and those of the compound which it contains have also been defined above.

To make the subject of the invention better understood, several embodiments, are described below, by way of examples which are purely illustrative and do not imply any limitation.

EXAMPLE 1

250 mg of 2-nitro-para-phenylenediamine are dissolved in 10 ml of absolute ethanol. The solution is made up to 100 ml with a pH 10 ammonia buffer solution. The concentration of 2-nitro-para-phenylenediamine is 0.016 mole per liter.

100 mg of cut hair, approximately 2 cm in length, is weighed out. It is placed in a 10-ml beaker. 5 ml of the 2-nitro-para-phenylenediamine solution, previously maintained at 30° C., are added and left in contact for 2 minutes at 30° C. The whole is poured into a frustoconical filter funnel, of porosity 4. Vacuum suction is applied for 2 minutes, while the hair is distributed well on the sinter with a glass rod.

The hair is transferred into a 25-ml beaker. 10 ml of the pH 10 ammonia buffer solution are added. The materials are left in contact for 30 minutes at 30° C. The solution is transferred into a 25-ml graduated flask. This operation is repeated a second time. The solution is made up to 25 ml with the pH 10 buffer solution. The absorbance at 470 nm is read off on the spectrophotometer.

Calibration range 2 ml of the 2-nitro-para-phenylenediamine solution are taken and made up to 25 ml with the pH 10 buffer solution. 1 ml, 2 ml and 3 ml of this solution are taken in succession and made up each time to 25 ml with the pH 10 buffer solution. The absorbance of each solution at 470 nm is read off. The calibration curve is plotted.

Results

The results are expressed on a colorimetric scale or on a scale of concentrations of the uncharged compound, as shown in the table below, from which it is concluded that the hair studied belongs to one of the types 1 to 9, these types being defined according to the table.

TABLE

| | Molar absorbance of 2-nitro-para-phenylenediamine: 4000 | | | | | | | | |
|---|---|---|---|---|---|---|---|---|---|
| | Hair 1 | Hair 2 | Hair 3 | Hair 4 | Hair 5 | Hair 6 | Hair 7 | Hair 8 | Hair 9 |
| Solution | 0.29 | 0.51 | 0.57 | 0.67 | 0.52 | 0.92 | 0.89 | 1.01 | 1.24 |

TABLE-continued

| Molar absorbance of 2-nitro-para-phenylenediamine: 4000 | | | | | | | | | |
|---|---|---|---|---|---|---|---|---|---|
| | Hair 1 | Hair 2 | Hair 3 | Hair 4 | Hair 5 | Hair 6 | Hair 7 | Hair 8 | Hair 9 |
| absorbance Concentration (μmoles of dye per 100 mg of hair) | 1.8 | 3.2 | 3.6 | 4.2 | 3.3 | 6.0 | 5.8 | 6.3 | 7.8 |

Hair 1: natural hair
Hair 2: weak bleached hair
Hair 3: medium bleached hair
Hair 4: strong bleached hair
Hair 5: natural hair + 1 permanent wave
Hair 6: natural hair + 3 permanent waves
Hair 7: weak bleached hair + 1 permanent wave
Hair 8: medium bleached hair + 1 permanent wave
Hair 9: strong bleached hair + 1 permanent wave

EXAMPLE 2

250 mg of 2-nitro-para-phenylenediamine are dissolved in 10 ml of absolute ethanol. The solution is made up to 100 ml with a pH 10 ammonia buffer solution.

A 5-ml plastic syringe, 1 cm in diameter, is modified by inserting a plastic grid at the bottom of the syringe body. The end of the syringe, which receives the needle in normal use, is removed so as to eliminate any dead volume. A quantity of hair of between 20 and 30 mg is introduced into the syringe. This hair is taken, unweighed, from a head, for comparison with a reference lock. The syringe plunger is zeroed. 2 ml of the colored solution of 2-nitro-para-phenylenediamine are drawn in by pulling the plunger up to the syringe mark. The materials are left in contact for exactly 2 minutes at ambient temperature. The liquid is discarded. The end of the syringe is wiped. 5 ml of a pH 10 ammonia buffer solution are drawn in. This solution is immediately discarded. The end of the syringe is wiped again. 5 ml of a pH 10 ammonia solution are drawn in and left in contact for 5 minutes at ambient temperature. The liquid is collected in a test tube.

The color is compared to two reference tubes A and B of a red dye. The reference tube A contains 5 ml of a solution of 7.7 mg of 2-nitro-para-phenylenediamine per liter of pH 10 ammonia buffer solution (sealed tube); the absorbance is 0.20; this reference tube A represents the upper limit of state 1. The reference tube B contains 5 ml of a solution of 26.5 mg of 2-nitro-para-phenylenediamine per liter of pH 10 ammonia buffer (sealed tube); the absorbance is 0.69; this reference tube B represents the lower limit of state 3.

Any color included between the reference tubes A and B is considered to belong to state 2.

The results are expressed as follows:
state 1 corresponds to natural hair, that is to say hair with little sensitization;
state 2 corresponds to hair which has undergone a single cosmetic treatment (a bleaching or a permanent wave or a dyeing), that is to say intermediately sensitized hair;
state 3 corresponds to hair which has been subjected to multiple, repeated or combined cosmetic treatments (bleaching+permanent wave or repeated permanent waves), that is to say to highly sensitized hair.

This classification is highly useful, for example for the hairdresser, who can thus readily control the operating conditions of a bleaching (application time, oxidant concentration, etc.) or of a permanent waving (strength of the reducing liquid) as a function of the quality of the customer's hair.

EXAMPLE 3

830 mg of "HC Blue 2" dye are dissolved in 10 ml of absolute ethanol. The solution is made up to 100 ml with a pH 10 ammonia buffer solution. The concentration of "HC Blue 2" is 0.029 mole per liter.

100 mg of cut hair, approximately 2 cm in length, are weighed out. They are placed in a 10-ml beaker. 5 ml of the "HC Blue 2" solution, previously maintained at 30° C. are added. The materials are left in contact for 2 minutes at +° C. The whole is poured into a frustoconical filter funnel, of porosity 4. Vacuum suction is applied for 2 minutes while the hair is distributed well on the sinter with a glass rod.

The hair is transferred to a 25-ml beaker. 10 ml of the pH 10 ammonia buffer solution are added and the materials are left in contact for 30 minutes at 30° C. The solution is transferred to a 25-ml graduated flask. This operation is repeated a second time. The solution is made up to 25 ml with the pH 10 buffer solution. The absorbance at 540 nm is read off on the spectrophotometer.

The results can be expressed on a sensitization scale defined as follows:

| | |
|---|---|
| Natural hair, with very little sensitization, | mark 10 - absorbance: 0.15 |
| Highly sensitized hair: | mark 100 - absorbance: 1.05 |

The degree of sensitization of the hair is then obtained using the following formula:

$$S = 100 \left( \frac{100 \times A}{TS} \right) - K$$

in which A denotes the absorbance of the extraction solution, TS the hair test specimen in mg, i.e. approximately 100, K a constant which is equal to 5 under the conditions of this test.

Finally, the results are expressed on a colorimetric scale or on this sensitization scale, as indicated in the following table, from which it is concluded that the hair studied belongs to one of the types 1 to 9, which have been defined in Example 1.

TABLE

| Molar absorbance of "HC Blue 2": 3500 | | | | | | | | |
| --- | --- | --- | --- | --- | --- | --- | --- | --- |
| Hair 1 | Hair 2 | Hair 3 | Hair 4 | Hair 5 | Hair 6 | Hair 7 | Hair 8 | Hair 9 |
| Solution absorbance | | | | | | | | |
| 0.15 | 0.22 | 0.30 | 0.42 | 0.23 | 0.53 | 0.50 | 0.77 | 1.10 |
| Degree of sensitization | | | | | | | | |
| 10 | 17 | 25 | 37 | 18 | 48 | 45 | 72 | 105 |

EXAMPLE 4

830 mg of "HC Blue 2" dye are dissolved in 10 ml of absolute ethanol. The solution is made up to 100 ml with the pH 10 ammonia buffer solution.

Approximately 25 mg of hair (between 20 and 30 mg of hair taken from a head) are introduced, unweighed, for comparison with a reference lock, into a syringe modified as in Example 2. 2 ml of a colored solution of "HC Blue 2" are drawn in by pulling the piston up to the syringe mark. The materials are left in contact for exactly 2 minutes at ambient temperature. The liquid is discarded and the end of the syringe is wiped. 5 ml of a pH 10 ammonia buffer solution are drawn in. This solution is immediately discarded and the end of the syringe is wiped. 5 ml of pH 10 ammonia buffer solution are drawn in and left in contact for 5 minutes at ambient temperature. The liquid is collected in a test tube.

The color is compared to a color scale prepared once and for all, comprising degrees of blueness ("HC Blue 2" dye shade).

The upper limit of state 1 is placed at the scale level at a color intensity which is similar to a solution of 16.4 mg of "HC Blue 2" per liter of pH 10 ammonia buffer (absorbance: 0.20).

The lower limit of state 3 is placed at the scale level at a color intensity similar to that of a solution of 43.9 mg of "HC Blue 2" per liter of pH 10 ammonia buffer solution (absorbance: 0.54).

The results are similar to those obtained in Example 2.

EXAMPLE 5

The method used is the same as that described in Example 2. The only modification involves the extraction time at the end of the test. In this case, this time is 3 minutes at ambient temperature. In order to retain the same distribution of hair in states 1, 2 and 3, the reference tubes A and B have to be modified as follows:

the reference tube A now has an absorbance of 0.16 (5 ml of a solution of 6.1 mg of 2-nitro-paraphenylenediamine per liter of ammonia buffer).

the reference tube B now has an absorbance of 0.52 (5 ml of a solution of 19.9 mg of 2-nitro-paraphenylenediamine per liter of ammonia buffer).

EXAMPLE 6

The method used is the same as that described in example 2. The only modification involves the time of contact between hair and the colored solution (first part of the test). This time is 1 minute (at ambient temperature) in this case. The extraction time at the end of the test is similar to that in Example 2, namely 5 minutes. In order to retain the same distribution of hair in states 1, 2 and 3, the reference tubes A and B must be modified as follows:

the reference tube A now has an absorbance of 0.14 (5ml of a solution of 5.4 mg of 2-nitro-paraphenylenediamine per liter of ammonia buffer).

the reference tube B now has an absorbance of 0.40 (5 ml of a solution of 15.3 mg of 2-nitro-paraphenylenediamine per liter of ammonia buffer).

EXAMPLE 7

800 mg of 2-N-(β-aminoethyl)amino-5-N,N-bis(β-hydroxyethyl)aminonitrobenzene are dissolved in 100 ml of pH 10 ammonia buffer solution. The concentration of 2-N-(β-aminoethyl)amino-5-N,N-bis(β-hydroxyethyl)aminonitrobenzene is 0.028 mole per liter.

A quantity of hair of between 30 and 60 mg is introduced into the syringe, modified as in Example 2. 2 ml of previously prepared colored solution are drawn in by pulling the plunger up to the syringe mark. The materials are left in contact for exactly 2 minutes at ambient temperature. The liquid is discarded and the end of the syringe is wiped. 5 ml of pH 10 ammonia buffer solution are drawn in. This solution is immediately discarded and the end of the syringe is wiped. 5 ml of pH 10 ammonia buffer solution are then drawn in and left in contact for 5 minutes at ambient temperature. The liquid is collected in a test tube.

The color is compared to two reference tubes A and B (blue color). Molar absorbance of 2-N-(β-aminoethyl)amino-5-N,N-bis(β-hydroxyethyl)aminonitrobenzene: 2500. Tube A contains 5 ml of a solution of 18 mg of dye per liter of pH 10 ammonia buffer (sealed tube); the absorbance is 0.16; this reference tube A represents the upper limit of state 1. Reference tube B contains 5 ml of a solution of 42.6 mg of dye per liter of pH 10 ammonia buffer (sealed tube); the absorbance is 0.38; this reference tube B represents the lower limit of state 3.

Any color included between the reference tubes A and B is considered to belong to state 2.

The results are similar to those obtained in Example 2.

EXAMPLE 8

300 mg of 4-N-(β-hydroxyethyl)amino-3-nitroaniline are dissolved in 10 ml of absolute ethanol. The solution is made up to 100 ml with a pH 10 ammonia buffer solution. The concentration of 4-N-(β-hydroxyethyl)amino-3-nitroaniline is 0.015 mole per liter.

100 mg of cut hair, approximately 2 cm in length are weighed out. They are placed in a 10-ml beaker. 5 ml of the dye solution, previously maintained at 30° C., are added. The materials are left in contact for 2 minutes at 30° C. The whole is poured into a frustoconical filter funnel of porosity 4. Vacuum suction is applied for 2 minutes, while the hair is distributed well on the sinter with a glass rod.

The hair is transferred into a 25-ml beaker. 10 ml of the pH 10 ammonia buffer solution are added and left in contact for 30 minutes at 30° C. The solution is transferred to a 25-ml graduated flask. The operation is repeated a second time. The solution is made up to 25 ml with the pH 10 buffer solution. The absorbance at 505 nm is read off on a spectrophotometer.

Calibration range 2 ml of the 4-N-(β-hydroxyethyl)amino-3-nitroaniline are taken. They are made up to 20 ml with the pH 10 buffer solution. 0.5 ml, 1 ml and 2 ml of this solution are taken in succession and made up each time to 25 ml with the pH 10 buffer solution. The absorbance of each solution at 505 nm is read off. The calibration curve is plotted.

Results

The results are expressed on a colorimetric scale or on a concentration scale, as indicated in the following table, from which it is concluded that the hair studied belongs to one of the types 1 to 9, which have been defined in Example 1.

TABLE

| Molar absorbance of 4-N—($\beta$-hydroxyethyl)amino-3-nitro-aniline: 4200 | | | | | | | | | |
|---|---|---|---|---|---|---|---|---|---|
| | Hair 1 | Hair 2 | Hair 3 | Hair 4 | Hair 5 | Hair 6 | Hair 7 | Hair 8 | Hair 9 |
| solution absorbance | 0.16 | 0.33 | 0.37 | 0.41 | 0.35 | 0.50 | 0.48 | 0.55 | 0.64 |
| concentration ($\mu$moles of dye per 100 mg of hair) | 1 | 2 | 2.2 | 2.4 | 2.1 | 3.1 | 3 | 3.4 | 4 |

EXAMPLE 9

800 mg of 2-N-methylamino-5-N,N-bis($\beta$-hydroxyethyl)aminonitrobenzene are dissolved in 10 ml of absolute ethanol. The solution is made up to 100 ml with pH 10 ammonia buffer solution. The concentration of 2-methylamino-5-N,N-bis($\beta$-hydroxyethyl)aminonitrobenzene is 0.031 mole per liter.

40 mg of hair is placed in the syringe, modified as in Example 2. 5 ml of the previously prepared colored solution are drawn in by pulling the piston up to the syringe mark. The materials are left in contact for exactly 2 minutes at ambient temperature. The liquid is discarded and the end of the syringe is wiped. 2 ml of pH 10 ammonia buffer are drawn in. This solution is immediately discarded and the end of the syringe is wiped. This operation is repeated a second time, namely the drawing in of 2 ml of buffer solution and immediate discarding. Next, 5 ml of pH 10 ammonia buffer solution are drawn in and left in contact for 15 minutes at ambient temperature. The liquid is collected in a test tube. 5 ml of pH 10 ammonia buffer solution are drawn in again and left in contact for 5 minutes at ambient temperature. The liquid is collected in the same test tube as before.

The color is compared to the two reference tubes A and B (blue color). Molar absorbance of 2-N-methylamino-5-N,N-bis($\beta$-hydroxyethyl)aminonitrobenzene: 3800.

Reference tube A, which represents the upper limit of state 1, contains 10 ml of a solution of 9.4 mg of dye per liter of pH 10 ammonia buffer (sealed tube); the absorbance is 0.14.

Reference tube B, which represents the lower limit of state 3, contains 5 ml of a solution of 18.1 mg of dye per liter of pH 10 ammonia buffer (sealed tube); the absorbance is 0.27.

Any color included between the reference tubes A and B is considered to belong to state 2.

The results are similar to those obtained in Example 2.

EXAMPLE 10

244 mg of 2,6-dimethylphenol are dissolved in 5 ml of absolute ethanol. The solution is made up to 100 ml with a pH 4.7 acetate buffer solution. The concentration of 2,6-dimethylphenol is 0.02 mole per liter.

100 mg of cut hair, approximately 2 cm in length, are weighed out. They are placed in a 10-ml beaker. 5 ml of the solution of 2,6-dimethylphenol, previously maintained at 30° C., are added. The materials are left in contact for 2 minutes at 30° C. The whole is poured into a frustoconical filter funnel of porosity 4. Vacuum suction is applied for 2 minutes while the hair is distributed well on the sinter with a glass rod. The hair is transferred to a 25-ml beaker. 10 ml of water are added and left in contact for 30 minutes at 30° C. The solution is transferred to a 25-ml graduated flask. This operation is repeated a second time and the solution is made up to 25 ml with water.

Development 2 ml of pH 10 ammonia buffer, 2 ml of a solution containing 34.6 mg of para-phenylenediamine per liter of water and 0.2 ml of a solution containing 3 g of potassium ferricyanide per liter of water are added in succession to 1 ml of the extraction solution. The color is allowed to develop for 10 minutes. The absorbance at 525 nm is read off on a spectrophotometer compared to that of a control prepared as above, but with the extraction solution replaced by 1 ml of water.

Calibration range 48.8 mg of 2,6-dimethylphenol are dissolved in 50 ml of water. 1 ml of this solution is taken three times in succession and made up with water to 25 ml, 50 ml and 100 ml successively.

1 ml of these three latter solutions is taken successively, and in each case 2 ml of pH 10 ammonia buffer are added, followed by 2 ml of the para-phenylenediamine solution and 0.2 ml of the potassium ferricyanide solution.

The color is allowed to develop for 10 minutes. The absorbance at 525 nm is read off on the spectrophotometer compared to a control prepared by replacing the 2,6-dimethylphenol solutions with 1 ml of water. The calibration curve is plotted.

Results

The results are expressed on a colorimetric scale or on a concentration scale, as indicated in the following table, from which it is concluded that the hair studied belongs to one of the types 1 to 9, which have been defined in Example 1.

TABLE

| Molar absorbance of 2,6-dimethylphenol under the conditions of development: 1750 | | | | | | | | | |
|---|---|---|---|---|---|---|---|---|---|
| | Hair 1 | Hair 2 | Hair 3 | Hair 4 | Hair 5 | Hair 6 | Hair 7 | Hair 8 | Hair 9 |
| Solution | 0.20 | 0.25 | 0.32 | 0.36 | 0.33 | 0.51 | 0.46 | 0.57 | 0.67 |

TABLE-continued

| Molar absorbance of 2,6-dimethylphenol under the conditions of development: 1750 | | | | | | | | | |
|---|---|---|---|---|---|---|---|---|---|
| | Hair 1 | Hair 2 | Hair 3 | Hair 4 | Hair 5 | Hair 6 | Hair 7 | Hair 8 | Hair 9 |
| absorbance Concentration ($\mu$moles of reactant per 100 mg of hair) | 2.9 | 3.6 | 4.6 | 5.2 | 4.7 | 7.3 | 6.7 | 8.2 | 9.6 |

EXAMPLE 11

288 mg of α-naphthol are dissolved in 15 ml of absolute ethanol. The solution is made up to 100 ml with a pH 4.7 acetate buffer solution. The concentration of α-naphthol is 0.02 mole per liter.

100 mg of cut hair, approximately 2 cm in length, are weighed out. They are placed in a 10-ml beaker. 5 ml of the α-naphthol solution, previously maintained at 40° C., are added. The materials are left in contact for 2 minutes at 40° C. The whole is poured into a frustoconical filter funnel of porosity 4. Vacuum suction is applied for 2 minutes while the hair is distributed well on the sinter with a glass rod. The hair is transferred to a 25-ml beaker. 10 ml of water are added and left in contact for 30 minutes at 40° C. The solution is transferred to a 25-ml graduated flask. This operation is repeated a second time and the solution is made up to 25 ml with water.

Development 2 ml of concentrated sulphuric acid, 0.1 ml of a solution of glyoxal at a concentration of 5 g per 100 ml of water, prepared at the time of use, and 1 ml of the solution to be developed are placed in succession in a test tube. The absorbance at 615 nm is read off on a spectrophotometer, compared to a control prepared as above, but with the solution to be developed replaced by 1 ml of water.

Calibration scale 57.5 ml of α-naphthol are dissolved in 2 ml of absolute ethanol and water up to a total volume of 50 ml. 1 ml of this solution is taken three times in succession and is made up with water to 25 ml, 50 ml and 100 ml successively. 2 ml of concentrated sulphuric acid, 0.1 ml of the glyoxal solution and 1 ml of one of the three above solutions are placed successively in a test tube. The same procedure is carried out in two other test tubes using the two other above solutions. The absorbance at 615 nm is read off on a spectrophotometer, compared to a control prepared by replacing the α-naphthol solutions with 1 ml of water. The calibration curve is plotted.

Results

The results are expressed on a colorimetric scale or on a concentration scale, as indicated in the following table, from which it is concluded that the hair studied belongs to one of the types 1 to 9, which have been defined in Example 1.

TABLE

| | Molar absorbance of α-naphthol under the development conditions: 4500 | | | | | | | | |
|---|---|---|---|---|---|---|---|---|---|
| | Hair 1 | Hair 2 | Hair 3 | Hair 4 | Hair 5 | Hair 6 | Hair 7 | Hair 8 | Hair 9 |
| Solution absorbance | 0.53 | 0.75 | 0.81 | 0.92 | 0.76 | 1.23 | 1.16 | 1.30 | 12.54 |
| Concentration ($\mu$moles of α-naphthol per 100 mg of hair) | 2.8 | 4.9 | 4.3 | 4.9 | 4.1 | 6.6 | 6.2 | 6.9 | 8.2 |

EXAMPLE 12

526 mg of 2,4-diaminoanisole sulphate (compound crystallized with 1.5 moles of $H_2O$) are dissolved in 100 ml of pH 10 ammonia buffer. The concentration of 2,4-diaminoanisole sulphate is 0.02 mole per liter.

100 mg of cut hair, approximately 2 cm in length, are weighed out. They are placed in a 10-ml beaker. 5 ml of the 2,4-diaminoanisole sulphate solution, previously maintained at 30° C., are added. The materials are left in contact for 2 minutes at 30° C. The whole is poured into a frustoconical filter funnel of porosity 4. Vacuum suction is applied for 2 minutes while the hair is distributed well on the sinter with a glass rod. The hair is transferred to a 25-ml beaker. 10 ml of pH 10 ammonia buffer are added and left in contact for 30 minutes at 30° C. The solution is transferred to a 25-ml graduated flask. This operation is repeated a second time and the solution is made up to 25 ml with the pH 10 ammonia buffer.

Development 2 ml of pH 10 ammonia buffer, 2 ml of a solution containing 34.6 mg of para-phenylenediamine per liter of water, and 0.15 ml of a solution containing 3 g of potassium ferricyanide per liter of water are added in succession to 2 ml of the extraction solution. The color is allowed to develop for 10 minutes. The absorbance at 515 nm is read off on a spectrophotometer, compared to a control prepared as before, but with the extraction solution replaced by 200 ml of pH ammonia buffer.

Calibration scale 210.4 mg of 2,4-diaminoanisole sulphate are dissolved in 100 ml of pH 10 ammonia buffer. 1 ml of this solution is taken three times in succession and made up with pH 10 ammonia buffer to 25 ml, 50 ml and 100 ml successively. 2 ml of one of three above solutions, 2 ml of pH 10 ammonia buffer, 2 ml of the para-phenylenediamine solution and 0.15 ml of the potassium ferricyanide solution are placed in succession in a test tube. The same is done in two other test tubes with the two other solutions above.

The color is allowed to develop for 10 minutes. The absorbance at 515 nm is read off on a spectrophotometer, compared to a control prepared as before, but with the 2,4-diaminoanisole sulphate solutions replaced by 2 ml of pH 10 ammonia buffer. The calibration curve is plotted.

Results

The results are expressed on a colorimetric scale or on a concentration scale, as indicated in the following table, from which it is concluded that the hair studied belongs to one of the types 1 to 9, which have been defined in Example 1.

TABLE

| | Molar absorbance of 2,4-diaminoanisole sulphate under the development conditions: 2300 | | | | | | | | |
|---|---|---|---|---|---|---|---|---|---|
| | Hair 1 | Hair 2 | Hair 3 | Hair 4 | Hair 5 | Hair 6 | Hair 7 | Hair 8 | Hair 9 |
| Solution absorbance | 0.18 | 0.21 | 0.25 | 0.27 | 0.26 | 0.42 | 0.39 | 0.46 | 0.51 |
| Concentration ($\mu$moles of reactant per 100 mg of hair) | 1.9 | 2.2 | 2.6 | 2.8 | 2.7 | 4.2 | 4.1 | 4.8 | 5.3 |

EXAMPLE 13

256 mg of 1,3-dihydroxynaphthalene are dissolved in 10 ml of absolute ethanol. The solution is made up to 100 ml with a pH 4.7 acetate buffer solution. The concentration of 1,3-dihydroxynaphthalene is 0.016 mole per liter. This solution is prepared at the time of use; it is kept at 30° C., in the absence of light.

100 mg of cut hair, approximately 2 cm in length, are weighed out. They are placed in a 10-ml beaker. 5 ml of the 1,3-dihydroxynaphthalene solution are added. The materials are left in contact for 2 minutes at 30° C. The whole is poured into a frustoconical filter funnel of porosity 4. Vacuum suction is applied for 2 minutes while the hair is distributed well on the sinter with a glass rod. The hair is transferred to a 25-ml beaker. 10 ml of water are added and left in contact for 30 minutes at 30° C. The solution is transferred to a 25-ml graduated flask. This operation is repeated a second time and the solutions are made up to 25 ml with water.

Development

One volume of a solution of $FeCl_3.6H_2O$ at a concentration of 3 g per liter of 0.4N HCl, 1 volume of a solution of potassium ferricyanide at a concentration of 3 g per liter of water, and 2 volumes of water are mixed before use. This reagent is kept in the absence of light. 0.5 ml of the extraction solution and 4 ml of the reagent are placed in a test tube. The color is allowed to stabilize for 10 minutes in the dark. The absorbance at 715 nm is read off on a spectrophotometer, compared to a control prepared as before but with the extraction solution replaced by 0.5 ml of water.

Calibration scale 64 mg of 1,3-dihydroxynaphthalene are dissolved in 50 ml of water. 1 ml of this solution is taken three times in succession and is made up with water to 25 ml, 50 ml and 100 ml successively. 0.5 ml of these three latter solutions is taken in succession. 4 ml of $FeCl_3$/potassium ferricyanide reagent are added in each case. The color is allowed to stabilize for 10 minutes in the dark. The absorbance at 715 nm is read off on a spectrophotometer, compared to a control prepared by replacing the 1,3-dihydroxynaphthalene solutions with 0.5 ml of water. The calibration curve is plotted.

Results

The results are expressed on a colorimetric scale or on a concentration scale, as indicated in the following table, from which it is deduced that the hair studied belongs to one of the types 1 to 9, which have been defined in Example 1.

TABLE

| | Molar absorbance of 1,3-dihydroxynaphthalene under the development conditions: 2500 | | | | | | | | |
|---|---|---|---|---|---|---|---|---|---|
| | Hair 1 | Hair 2 | Hair 3 | Hair 4 | Hair 5 | Hair 6 | Hair 7 | Hair 8 | Hair 9 |
| Solution absorbance | 0.38 | 0.50 | 0.68 | 0.77 | 0.70 | 1.1 | 1.0 | 1.23 | 1.6 |
| Concentration ($\mu$moles of reactant per 100 mg of hair) | 2.4 | 3.1 | 4.3 | 4.9 | 4.4 | 6.9 | 6.3 | 7.7 | 10.0 |

We claim:

1. A process for evaluating the state of the surface of keratinous fibres, comprising the steps of:
  (a) selecting a compound having an overall spatial size equal to the maximum dimension of the interstices present at the surface of the keratinous fibres, said compound being capable of dissolving in an aqueous medium, to form a colored solution or a solution capable of being colored by a development, said compound also being stable under the conditions of application of the process, and capable of being maintained at a pH such that no ionic charge appears;
  (b) preparing an aqueous immersion solution containing said compound;
  (c) immersing a specimen of the keratinous fibres whose surface state is to be evaluated in said immersion solution to permit said fibres to "take up" an amount of said compound which amount is a function of the state of the surface of the latter;
  (d) withdrawing said specimen from said immersion solution and removing the excess of said immersion solution saturating the fibres by quick washing or dewatering;
  (e) extracting said compound from the said specimen by immersing said specimen in at least one aqueous bath whose pH is substantially identical to that of said immersion solution, to produce an extract solution which is correspondingly colored or capable of being colored by a development;

(f) where necessary, developing the color of the extraction solution; and (g) deducing the state of the surface of said fibres from the quantity of said compound present in said extract solution.

2. A process according to claim 1, comprising, in step (a), selecting a compound which has a maximum overall size of $10^{-3}\mu$ and is sufficiently soluble in an aqueous medium to permit the preparation of a solution of the said compound containing at least 0.01 mole per liter, said compound also being capable of dissolving in an aqueous medium, to form a solution which, naturally or after colorimetric development, absorbs visible or ultraviolet light or both and whose molar absorbance, measured at the wavelength of the maximum of the absorption spectrum of the said solution which is colored naturally or after colorimetric development, is at least equal to 1500.

3. A process according to claim 1 comprising, in step (a), selecting a compound of the benzene or naphthalene series.

4. A process according to claim 3 comprising, in step (a), selecting, as a compound which does not require development, a compound of formula:

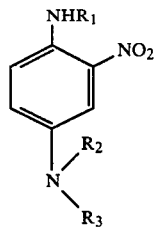
(I)

wherein
$R_1$ is H, $CH_2CH_2OH$, $CH_2CH_2NH_2$, or $CH_3$; and
$R_2$ and $R_3$ are the same or different and each is H or $CH_2CH_2OH$.

5. A process according to claim 3, comprising, in step (a), selecting, as a compound requiring development, 1,3-dihydroxynaphthalene; α-naphthol; 2,6-dimethylphenol or 2,4-diaminoanisole sulphate.

6. A process according to claim 1 comprising, in step (b), preparing an immersion solution of said compound containing an aqueous medium and water-miscible organic solvent the weight ratio of said aqueous medium to said organic solvent being at least equal to 80:20.

7. A process according to claim 6 wherein said organic solvent is ethanol and the weight ratio of aqueous medium to ethanol is about 90:10.

8. A process according to claim 1, comprising, in step (b), preparing said aqueous immersion solution comprising an aqueous buffer solution.

9. A process according to claim 8, wherein the immersion solution prepared in step (b) has a pH at least 2 pH units below or above the $pk_a$ of said compound.

10. A process according to claim 1 comprising, in step (c), immersing the specimen of keratinous fibres in a proportion of approximately 100 mg of fibres per 2 to 10 ml of said immersion solution for at most 20 minutes.

11. A process according to claim 10 wherein, in step (c), said specimen is immersed for from 2 to 5 minutes at about ambient temperature.

12. A process according to claim 7 comprising, in step (e), extracting said specimen in at least one bath of the same buffer solution as that which was used, in step (b), to prepare said immersion solution, or at least one bath of water brought to the same pH as that of said buffer solution.

13. A process according to claim 1 comprising, in step (e), extracting said specimen for at least 3 minutes.

14. Process according to claim 1, comprising, in step (g), comparing said extract solution, if necessary after development of its color, to a range of dilutions of a concentrated solution of said compound in the same medium as that which was used in step (e), or analyzing said extract solution, if necessary after development of its color, by means of a spectrophotometer or a colorimeter set to the wavelength of the maximum of the absorption spectrum of said extract solution if necessary after development of its color.

15. A process according to claim 1 comprising, in step (g) expressing the results on a colorimetric scale, on a compound concentration scale or on an empirical scale after calibration.

16. A process according to claim 1 wherein said keratinous fibres are human hair and body hair.

17. A composition for use in evaluating the state of the surface of keratinous fibres comprising an aqueous solution of a compound as defined in claim 1 said solution being maintained at a pH such that said compound is unchanged.

18. A composition according to claim 17 wherein said compound has a maximum overall size of $10^{-3}\mu$, is present in the solution in a concentration of at least 0.01 mole per liter, and is capable, naturally or after colorimetric development, of absorbing visible or ultraviolet light or both, the solution having a molar absorbance, measured at the wavelength of the maximum of the absorption spectrum of said solution, of at least 1500.

19. A composition according to claim 17 wherein said compound is selected from the benzene or naphthalene series.

20. A composition according to claim 19, wherein said compound does not require development and is a compound of formula (I):

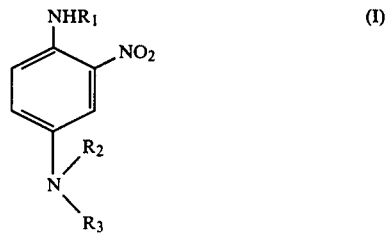
(I)

wherein:
$R_1$ is H, $CH_2CH_2OH$, $CH_2CH_2NH_2$, or $CH_3$; and
$R_2$ and $R_3$ are the same or different and each is H or $CH_2CH_2OH$.

21. A composition according to claim 19, wherein said compound requires development and is selected from 1,3-dihydroxynaphthalene, α-naphthol, 2,6-dimethylphenol and 2,4-diaminoanisole sulphate.

22. A composition according to claim 17 comprising an aqueous medium and a water-miscible organic solvent, the weight ratio of the aqueous medium to the organic solvent being at least equal to 80:20.

23. A composition according to claim 22 wherein said organic solvent is ethanol and the weight ratio of the aqueous medium to ethanol is about 90:10.

24. A composition according to claim 17 wherein the aqueous solution comprises a buffer solution and has a pH at least 2 pH units below or above the $pK_a$ of said compound.

* * * * *